United States Patent [19]

Zanakis et al.

[11] Patent Number: 4,774,967

[45] Date of Patent: Oct. 4, 1988

[54] METHOD AND APPARATUS FOR MAMMALIAN NERVE REGENERATION

[75] Inventors: Michael F. Zanakis, Livingston, N.J.; Bruce J. Albala, White Plains, N.Y.; Philip A. Femano, Nutley, N.J.

[73] Assignee: American BioInterface Corporation, New York, N.Y.

[21] Appl. No.: 905,787

[22] Filed: Sep. 9, 1986

[51] Int. Cl.$^4$ .......................... A61N 1/05; A61N 1/18
[52] U.S. Cl. .................................. 128/785; 128/419 R
[58] Field of Search .................... 128/784, 785, 419 C, 128/642, 419 R

[56] References Cited

U.S. PATENT DOCUMENTS

| | | | |
|---|---|---|---|
| 3,157,181 | 11/1964 | McCarty | 128/784 |
| 3,822,708 | 7/1974 | Zilber | 128/784 |
| 3,955,560 | 5/1976 | Stein et al. | 128/642 |
| 4,046,141 | 9/1977 | DeLuca | 128/642 |
| 4,306,561 | 12/1981 | Medinaceli | 128/303.13 |
| 4,623,355 | 11/1986 | Sawruk | 128/642 X |
| 4,628,942 | 12/1986 | Sweeney et al. | 128/784 |
| 4,632,116 | 12/1986 | Rosen et al. | 128/419 R |

FOREIGN PATENT DOCUMENTS

WO85/01213  3/1985  PCT Int'l Appl. .

OTHER PUBLICATIONS

Julien et al, "Electroneurographic Recordings . . . ", J. Neuroscience Methods, 5, No. 3, Mar. 1982, 267-272.
Politis et al.; Electromyographic Evaluation of a Novel Surgical Preparation, etc.; Experimental Neurology 87, 326-333 (1985).
Politis et al.; Tropism in Nerve Regeneration in Vivo, etc.; Brain Research, 253 (1982), 1-12.
Lundborg et al.; Nerve Regeneration in Silicone Chambers, etc.; Experimental Neurology 76, 361-375 (1982).
Madison et al.; Nontoxic Nerve Guide Tubes Support Neovascular Growth etc.; Experimental Neurology 86, 448-461 (1984).
Azzam et al.; Regeneration of Central Nervous System Axons etc., Experimental Neurology 89, 634-644 (1985).
Borgens et al.; Transected Dorsal Column Axons Within the Guinea Pig etc.; Journal of Comparative Neurology 250: 168-180 (1986).
Borgens, R. B.; The Role of Natural and Applied Electric Fields etc.; Ionic Currents in Development, 239-250 (1986).
Patel et al.; Orientation of Neurite Growth by Extracellular Electric Fields; The Journal of Neuroscience, vol. 2, No. 4, 483-496, Apr. 1982.
Patel et al.; Perturbation of the Direction of Neurite Growth etc., The Journal of Neuroscience, vol. 4, No. 12, 2939-2947, 12/84.
Kerns et al.; Effects of D.C. Electrical Stimulation etc., Abstracts-AAA 9th Annual Meeting.
Freeman et al.; Growth Cones of Goldfish Retinal Neurites etc., Axonal Growth and Guidance, 178.15.
Wilson et al.; Experimental Regeneration in Peripheral Nerves etc.; Paraplegia (1976), 14, 12-20.
Bassett, C. A. L.; Effects of Pulsed Electromagnetic Fields etc.; CNS Trauma 1 (1), 1984.
Young, W.; Pulsed Electromagnetic Fields Alter Calcium etc.; CNS Trauma 1 (1), 1984.
Schwartz et al.; Neuritic Outgrowth From Regenerating Goldfish etc., Birth Defects: Original Article Series, vol. 19, No. 4, 451-456, 1983.

(List continued on next page.)

Primary Examiner—Lee S. Cohen
Attorney, Agent, or Firm—Amster, Rothstein & Ebenstein

[57] ABSTRACT

The invention relates to method and apparatus for in vivo mammalian nerve regeneration of a damaged nerve using an electric current through the damaged nerve while the nerve ends are abutted against one another, sutured together or spaced apart from each other. The apparatus is implantable in a human body so that the electric current can be maintained for an extended period of time to produce regeneration of the damaged nerve.

OTHER PUBLICATIONS

Nuccitelli et al.; Embryonic Cell Motility Can Be Guided etc.; Exp. Cell. Res. 147 (1983).

Laub et al.; Actin Polymerization Induced by Pulsed Electric etc., Biochimica et Biophysica Acta., 803 (1984), 308–313.

Binderman et al.; Stimulation of Skeletal–Derived Cell Cultures etc., Biochemica et Biophysica Acta, 844 (1985), 273–279.

Korenstein et al.; Capacitative Pulsed Electric Stimulation etc.; Biochemica et Biophysica Acta, 803 (1984), 302–307.

Pomeranz et al.; Effect of Applied Electrical Fields on Sprouting etc.; Brain Research, 303 (1984), 331–336.

Kort et al.; Effects of Pulsing Electromagnetic Fields etc.; 26th Annual ORS, Atlanta, Georgia, Feb. 5–7, 1980, p. 19.

Murray et al.; Pulsed Electromagnetic Fields and Peripheral Nerve etc.; Journal of Bioelectricity, 3 (1 & 2), 19–32 (1984).

O'Brien et al.; Effects of Pulsing Electromagnetic Fields on Nerve Regeneration etc.; Journal of Bioelectricity, 3 ( 1 & 2), 33–40, 1984.

Parker et al.; The Effects of Pulsed Electromagnetic Fields etc., 3rd Annual Brags, San Francisco, CA, Oct. 2–5, 1983, p. 18.

Raji et al.; Effects of High Peak Pulsed Electromagnetic Field etc., The Lancet, Aug. 21, 1982, pp. 444–445.

Taubes, Gary; An Electrifying Possibility; Discover, Apr. 1986, 24–37.

Kuhn et al.; Nerve Implant Prosthesis for Facilitating Peripheral Nerve Regeneration; Nat'l. Bur. Stand. Spec. Pub., No. 415, 1975, 91–98.

Borgens et al.; Bioelectricity and Regeneration etc.; Experimental Zoology, 200, 1977, 403–416.

Borgens et al.; Bioelectricity and Regeneration etc.; BioScience, vol. 29, No. 8, 1979, 468–474.

Borgens et al.; Enhanced Spinal Cord Regeneration in Lamprey etc.; Science, vol. 213, Aug. 7, 1981, 611–617.

Khan et al.; Spinal Cord Explants Cultured on Carbon Filaments etc.; Process OutGrowth, 1985, p. 587.

J. Ralof; Severed Nerve Regrows to Bridge a Gap; MIT, Sep. 21, 1985, p. 183.

Research Industries Corporation Annual Report 1985; Balanced Growth in Transdermal Drug Therapies and Specialized Hospital Disposables, 1986.

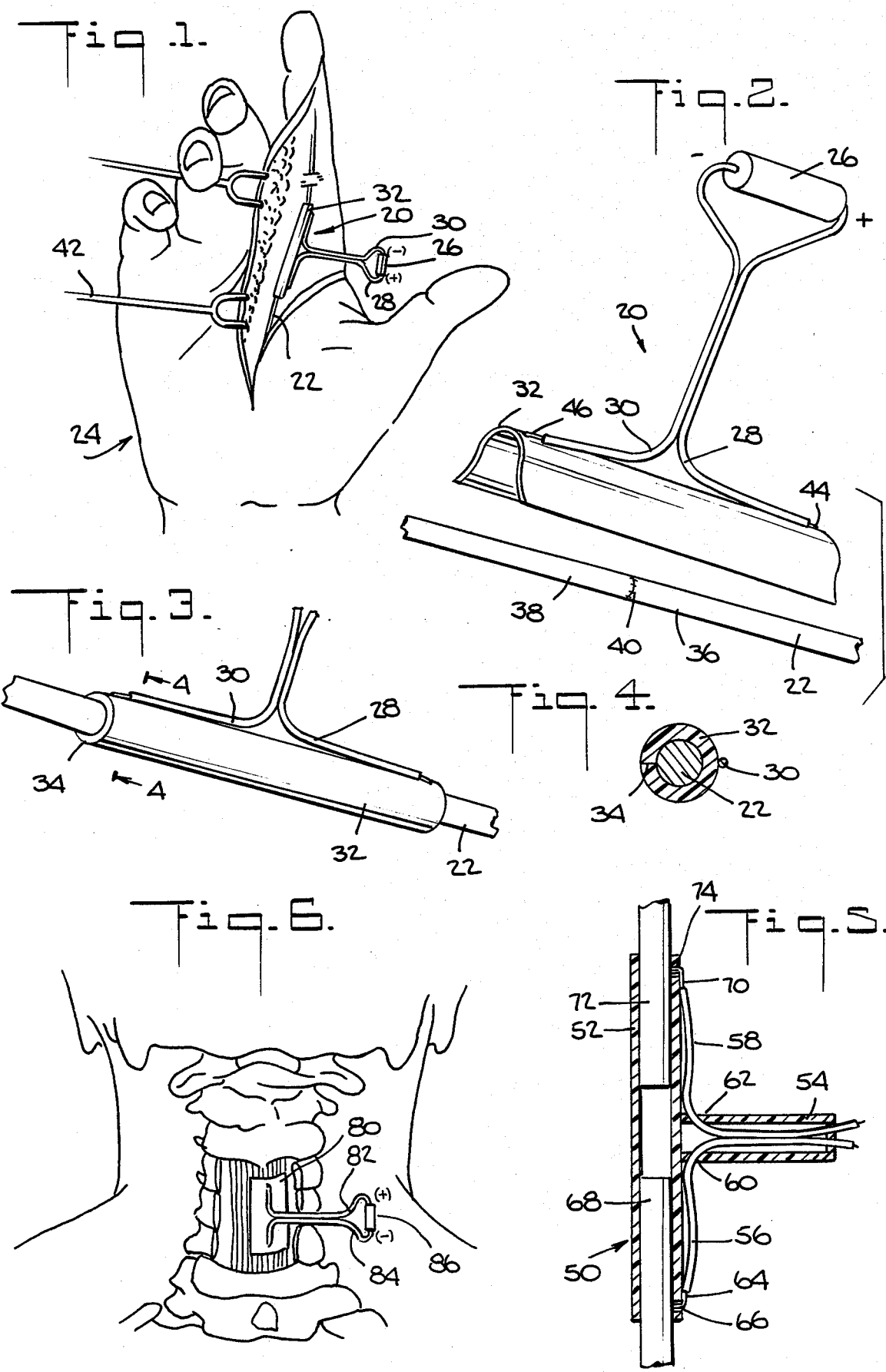

METHOD AND APPARATUS FOR MAMMALIAN NERVE REGENERATION

BACKGROUND OF THE INVENTION

The invention relates to the regeneration of a damaged mammalian nerve and particularly to a method and apparatus for in vivo mammalian nerve regeneration using an electric potential gradient or electric current established from the proximal nerve end (that is, the nerve end closest to the cell body) to the distal nerve end (that is, the nerve end furthest from the cell body) with the nerve ends either spaced apart from each other or sutured together.

Considerable research relating to nerve growth and nerve regeneration has produced numerous publications relating to these topics. The distinction between "nerve growth" and "nerve regeneration" is significant. The growth of a nerve does not assure that the nerve will function even partially as it did prior to damage. That is, "nerve growth" does not assure the functioning of the nerve as a channel for communication of information. In contrast, "nerve regeneration" as used herein is the regeneration of a nerve to serve at least partially as part of the communication system of the nervous system. It is well known in the art that there are substantial differences between a mammalian nervous system and other nervous systems. Thus, the evaluation of method and apparatuses for mammalian nerve regeneration must be carried out on a mammal to have any value and credibility.

When axons of the mammalian peripheral nervous system (PNS) are severely damaged (i.e., in compression or transection injuries), several phenomena may take place. First, if left unmodified, the distal stump will nearly always degenerate (Wallerian degeneration). This degeneration is associated with concomitant chromatolytic changes proximally in the perikaryon. If damage to the nerve is sufficiently severe, the axons in the proximal portion will degenerate, followed by the degeneration and (usually) death of the perikaryon. If the damage to the nerve is less severe and left unmodified, a number of biochemical changes begin to occur in the remaining proximal portion. These proximal changes involve a complex series of responses of the cell body to the injury which seem to prepare the intact portion for regeneration. Such changes include alterations in axonal transport characteristics, protein processing and nucleic acid synthesis. Morphologically regenerating growth cones from the damaged proximal stump often appear, and the axons will begin to regenerate from the proximal stump towards the original target region.

Such damage is likely to produce collateral sprouting from neighboring axons that are not as severly injured and which did not undergo Wallerian degeneration. The newly growing neurites probably use the degenerated distal segment as a guide to the denervated target area. Presumably, the reactive Schwann cells provide the communicative means for regeneration to the target by providing diffusable growth-promoting factors, and by providing a suitable growth surface established by the plasma membrane and/or basal lamina, or extracellular matrix. All of these morphological and biochemical changes are primarily dependent upon several factors, including the severity and location of the injury depending upon the proximity to the perikaryon, the size of the axons injured, and the species involved. For example, higher vertebrates have less capacity to regenerate the peripheral nervous system (PNS) axons effectively.

In the central nervous system (CNS), the unaided attempts at regeneration often are quickly aborted by the body, resulting in a completely degenerated proximal stump and perikaryon. Recent publications have improved the understanding of the cellular events in the CNS following injury. Transplantation of embryonic tissues into the brain or spinal cord has proven to be a useful tool for determining the essential factors for regeneration. Because embryonic cells have a high potential for growth and differentiation, their transplantation should provide a suitable environment capable of promoting and supporting growth of the lesioned adult central or peripheral nervous system. Fetal cell implants, particularly neurons and muscle fibers implanted into the nervous system, possess the ability to induce axons to grow with a strong attraction to the grafted fetal tissue. Much of the published work relating to transplantation has focused on attempts to induce regeneration in the CNS. The results from a large number of investigators have shown that, unlike the previous assumptions of past decades, parts of the CNS are indeed capable of limited regeneration. Both functional and morphological data suggest that the injured brain and spinal cord can recover a certain degree of function following trauma. The contribution of the graft to the reconstruction of the host CNS is not well established. For example, the role of collateral sprouting from undamaged fibers of the host into the damaged region containing the graft has not yet been determined. A major determinant of the extent of regeneration is the environment encountered by the regrowing axons. The mechanisms underlying the axonal growth, guidance, and maturation appear to be strongly influenced by trophic factors in the environment which are appropriate and necessary for regeneration and referred to in the art as "growth-promotors". These substances may be specific for a particular target tissue and are likely to have a wide spectrum of growth-promoting potencies.

The reason a moderate or severe injury to a mammalian nerve may not lead to appropriate innervation of the target tissue may be the proportionally greater distance (due to Wallerian degeneration) those axons must travel. Presumably, trophic substances from nearby tissues may have a greater trophic potential than the intended target tissue. As a result, gap length of an injury has been shown in the prior art to be a primary factor in determining the success of functional regeneration. This lack of target specificity has been suggested in the literature as the underlying cause of the frequent formation of neuromas, as well as the inappropriate contact on other tissues. Thus, significant improvements have been observed after neural anastomoses have been made. The current method of choice in neurosurgical repair of damage to peripheral nerves is simple anastomosing of the cut end of the nerve, although this intervention is limited.

Simple anastomosing will not be sufficient in those circumstances where damage and degeneration is so extensive that the distance between the remaining proximal and distal stumps is excessive. An alternative solution employs the use of a structure or "bridge" across the gap length from the cut proximal stump to either the distal portion of the nerve or to the target tissue itself. In animal studies, the various materials which have been used to bridge the gap include peripheral nerve grafts, mesothelial chambers, millipore and silicone tubes.

Of particular interest are the artificially produced and commercially available "nerve cuffs" or "nerve guide tubes" which are implanted and extend between the stumps. Prior art nerve guide tubes are electrically passive, that is, do not include any electrical current, and have the shape of a hollow cylinder. The nerve guide tubes are generally made of either silicon or bioresorbable substances. The nerve guide tubes can be filled or coated with a growth supporting matrix such as laminin that promotes neural growth over greater distances than the unmodified nerve guide tube alone. The nerve guide tubes have been studied, reported in the literature and are commercially available. During the regenerative process, between two and three weeks after injury, the host body usually causes the interior of the nerve guide tube to fill with a viscous fluid containing proteins and other material in an amorphous matrix. Protein strands appear oriented along the longitudinal axis of the chamber, and may serve as the substrate for cellular migration. Before axons appear, Schwann cells and fibroblasts infiltrate the matrix. In general, blood vessels appear last, although some studies have observed capillary formation prior to axonal growth. It has been suggested that the early invading cells modify the matrix of the nerve guide tube and thereby facilitate the ingrowth of axons. It is important to note that the extracellular matrix will form in the absence of a distal segment. No axonal outgrowth will occur, indicating that the matrix is by itself insufficient to promote axonal growth. Perhaps the distal stump provides a humoral agent diffusible in the matrix which is necessary for growth and/or guidance of axons. This would be similar to the requirement for Schwann cell or muscle cell "conditioned media" in the growth of sensory, sympathetic or motor neurons in vitro. Axon diameter and density are greater when a distal stump is present. Whatever the exact mechanisms responsible for growth, (structural, cellular, and/or humoral), and wherever the site of action (at the axon or its substratum), the nerve guide tubes provide an "artificial" environment suitable for supporting axonal growth over relatively long distances.

As used herein, a "nerve guide means" is an electrically passive physical structure for enhancing nerve regeneration and includes prior art nerve guide tubes and other structures which are not tubular such as a plate-shaped object, solid tubes and other shapes which are effective for enhancing nerve regeneration.

Some cell types have been shown to be affected by static and dynamic electromagnetic fields. Most extensively studied are the effects of electromagnetic fields on bone growth, and prior art reports of in vitro results have demonstrated beneficial effects to some specific types of cells. Recently, published studies in bone-derived cell cultures have shown that electromagnetic fields induce specific biochemical alterations. such effects include cAMP fluctuations, altered states of actin polymerization, enhanced DNA synthesis and changes in calcium uptake. The exact mechanisms responsible for electromagnetic field induced bone growth have not been characterized fully. Due to the complex morphology of the neuronal cell, as well as its ability to grow in vitro, the nervous system is particularly well-suited for studies of the effect of electromagnetic fields on the growth of cells. In the past ten years, many studies have demonstrated that neurite elongation and orientation can be influenced by an electromagnetic field. Specifically, within a static electric field, neurite growth is directed toward the cathode. Changes in the orientation of these neurites can be observed with light microscopy after a period of time from about several minutes to about several hours. All neurons that have been studied to date in vitro respond in some way to an applied electromagnetic field. Many variations in electromagnetic field parameters have been used to observe changes in neurite growth.

The vigorous in vitro response of all neuronal cell types to a wide range of electromagnetic field effects (and thus an apparent lack of specificity for cell type or stimulus) has been used as an argument against the concept that endogenous fields serve a primary role in the guidance of growing neuronal processes in vivo. This is often supported by studies showing neurite growth to a target in the absence of intrinsic action potentials, and axonal synaptogenesis occurring during the blockade of postsynaptic ion channels. Growth and guidance in the nervous system is complex. The local microenvironment with respect to the events required for growth and guidance must necessarily be important for the establishment of proper channels to the target cell. These events are multifactorial, and include a variety of bioelectrochemical processes, such as the timing of membrane interactions between growing axons and glia. It is likely that such multiple interactions are subtle, and may require extremely small local electrical interactions. Action potentials or postsynaptic events may therefore be insufficient alone, or temporarily inappropriate to affect the growth process significantly.

The method of application of the electromagnetic fields used in the in vitro studies is vastly different from what would be possible under local microenvironmental conditions. Typically, in vitro studies apply an electromagnetic field across a large population of cells, often in a culture dish having a volume of enormous size in comparison to the cell, and with a concomitantly applied homogenous current density. Experimental results substantiate that electromagnetic fields may serve a modulatory function in orienting neurite growth within localized regions.

The application of extracellular direct current electric fields in vitro may accelerate as well as orient the growth of neurites in embryonic explants or in dissociated neuronal cultures. The mechanisms by which these biochemical alterations occur are not well understood, nor are they necessarily directly related. In addition, different neuron types appear to respond differently with regard to stimulation amplitude and duration. The biophysical mechanism responsible may be related to the electrophoretic redistribution of cytoplasmic components which may occur if an extracellular potential produces a voltage potential drop in the cytoplasm. The site of most of the cell's electrical resistance is the plasma membrane so that the electromagnetic field would be the strongest and have the greatest voltage potential difference relative to the cytoplasm. Thus, an electromagnetic field may alter the membrane's voltage potential asymmetrically, thereby perturbing growth-controlling transport processes across the membrane. The cytoplasm has far less resistivity than the plasma membrane, and the voltage potential drop is on the order of $10^{-4}$ volts. The majority of work published involving electromagnetic fields on whole cells in vitro use a static electromagnetic field in the range of 0.1 to 15 V/cm, roughly translating into an average of 10 mv/cell diameter. Assuming that 50% of this voltage is exerted across the plasma membrane at each end of the cell, this would result in a hyperpolarization or depolarization of 5 mv, depending on the polarity. Most neuronal resting membrane potentials are approximately −70 to −90 mv and local ion conductances or enzyme activation states at the membrane may be changed enough to alter or modify the normal function.

Furthermore, an electrophoretic accumulation of molecules responsible for neuritic extension and/or adhesion may occur toward the membrane. A charged macromolecule of ordinary electrophoretic mobility (1 micron/sec/V/cm) across a 10 micron distance requires $10^4$ to $10^6$ seconds (three hours to ten days). It is possible that higher electromagnetic field strengths (approximately 10 V/cm) can cause substantial intracellular migration of growth-related molecules, or receptors for trophic substances. It has been shown in the prior art that the accumulation of surface glycoproteins can occur electrophoretically at the cathode in isolated cultured cells. Membrane glycoproteins are believed to play a crucial role in cell adhesion to the substratum. Cathodal accumulation of these molecules at the membrane may be responsible for some of the orienting effects of the electromagnetic field. These hypotheses are consistent with the majority of the prior art data showing that most changes in directionality or growth rate occur within twenty-four hours of exposure in vitro. Thus, an electromagnetic field in vitro produces a growth promotion effect as well as a guidance effect.

U.S. Pat. No. 4,306,561 discloses methods and apparatuses for the reattachment and repair of severed nerves in a human body. The '561 Patent describes the use of direct current stimulation of the nerve from the proximal nerve end to the distal nerve end to evoke an action potential (i.e. transmittance of electrical activity in the nerve) to test electrical continuity across the two juxtaposed nerve ends. The '561 patent does not, however, suggest the use of electric current as a means for regeneration of nerves. Further, the '561 patent strongly discourages suturing nerve ends together. The '561 patent discloses a device for holding the nerve ends in abutment which requires vacuum lines to engage the nerve ends and is generally in the form of a modified forceps. Thus, the device is not at all suitable for being implanted and the disclosure limits its use to a period of about 5 hours because the patient has an open wound during the use of the device. The requirement disclosed in the '561 patent that the nerve ends abut each other precludes the regeneration of a damaged nerve for which the nerve ends are spaced apart.

From the background given above, it can be appreciated that mammalian nerve regeneration and particularly peripheral nerve regeneration is a complex phenomenon. Furthermore, it can present serious problems to the neurosurgeon who wishes to intervene in some way to increase the chances of good functional recovery following severe damage to nerves, particularly to peripheral nerves.

SUMMARY OF THE INVENTION

The present invention relates to regeneration of a damaged mammalian nerve and overcomes these and other shortcomings of the prior art. As used herein, the word "nerve" means, generally, fibers of the central or peripherial nervous system. It is a primary object of the invention to provide a method and apparatus for in vivo mammalian nerve regeneration of a damaged nerve by applying an electric potential gradient from the proximal nerve end to the distal nerve end with the nerve ends either spaced apart from each other or sutured substantially in abutment to each other. As used herein, an "electric potential gradient from the proximal nerve end to the distal nerve end" is an electric voltage more positive at the proximal nerve end than the distal nerve end and is referred to as "correctly oriented" electric potential gradient.

It is a further object of the invention to provide a method and apparatus for in vivo mammalian nerve regeneration of a damaged nerve using an electric potential gradient from the proximal nerve end to the distal nerve end and a nerve guide means.

It is a still further object of the invention to provide a method and apparatus for in vivo mammalian nerve regeneration of a damaged nerve using an electric potential gradient from the proximal nerve end to the distal nerve end and a nerve guide means including a matrix conducive to the growth of nerve cells.

It is a yet further object of the present invention to provide an implantable apparatus for in vivo mammalian nerve regeneration of a damaged nerve.

In accordance with illustrative embodiments demonstrating objects and features of the present invention, there is provided one embodiment of the apparatus for in vivo mammalian nerve regeneration of a damaged nerve having proximal and distal nerve ends in which the apparatus includes means between the nerve ends to maintain the nerve ends in proximity to each other, and means to produce an electric potential gradient from the proximal nerve end to the distal nerve end at a level and for a period of time to regenerate the damaged nerve.

Another embodiment of the apparatus for in vivo mammalian nerve regeneration of a damaged nerve having proximal and distal nerve ends includes a nerve guide means extending between the nerve ends to induce nerve growth, and means to produce an electric potential gradient from the proximal nerve end to the distal nerve end at a level and for a time to regenerate the damaged nerve.

The invention also relates to one embodiment of a method of in vivo mammalian nerve regeneration of a damaged nerve having proximal and distal nerve ends in which the method includes suturing the nerve ends in substantial abutment to each other and thereafter, producing an electric potential gradient from the proximal nerve end to the distal nerve end at a level and for a period of time to regenerate the damaged nerve.

Additionally, the invention relates to another embodiment of a method for in vivo mammalian nerve regeneration of a damaged nerve having proximal and distal nerve ends in which the method includes means including positioning a nerve guide means near the nerve ends to enhance nerve growth and concurrently, producing an electric potential gradient from the proximal nerve end to the distal nerve end at a level and for a period of time to regenerate the damaged nerve.

The above descriptions, as well as further objects, features and advantages of the present invention will be more fully understood by reference of the following detailed description of the presently preferred, but nonetheless illustrative embodiments in accordance with the present invention, when taken in conjunction with the accompanying drawings.

BRIEF DESCRIPTION OF THE INVENTION

FIG. 1. is a perspective view of the front of a surgically opened human hand with an apparatus according to the invention applied to a damaged nerve in the hand;

FIG. 2 is a generally front perspective view on an enlarged scale of the apparatus shown in FIG. 1 as it is being engaged onto nerve ends sutured together, with the instrument holding the apparatus not shown for clarity in illustration;

FIG. 3 is a fragmentary perspective view of the apparatus shown in FIG. 2 after it has engaged the sutured nerve ends;

FIG. 4 is a sectional view along the line 4-4 shown in FIG. 3 and shows the damaged nerve encircled by the apparatus;

FIG. 5 is a sectional view of another embodiment of the apparatus enclosing spaced apart nerve ends;

FIG. 6 is a fragmentary perspective view of a spinal cord in a human neck with yet another embodiment of the apparatus, with portions of the neck omitted for clarity in illustration;

Figure 9:
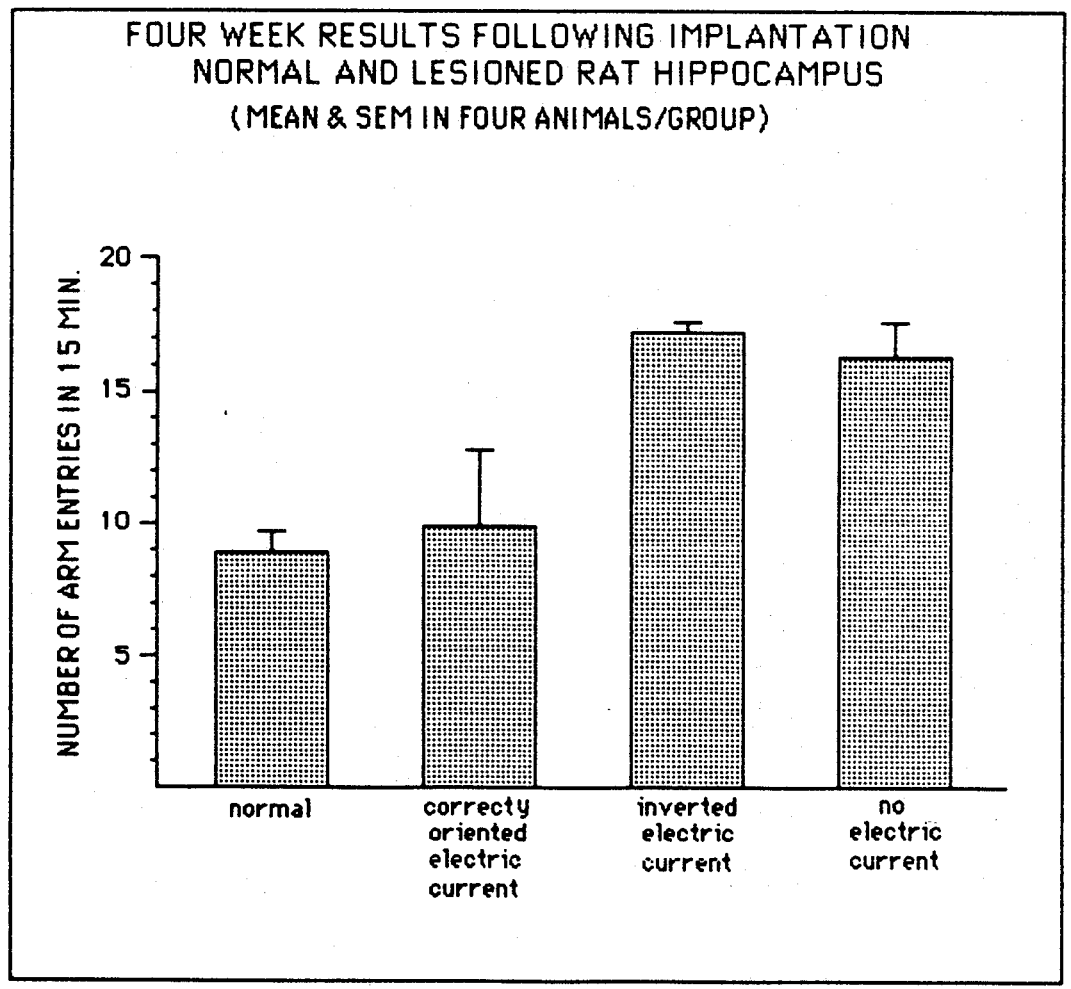
Figure 10:
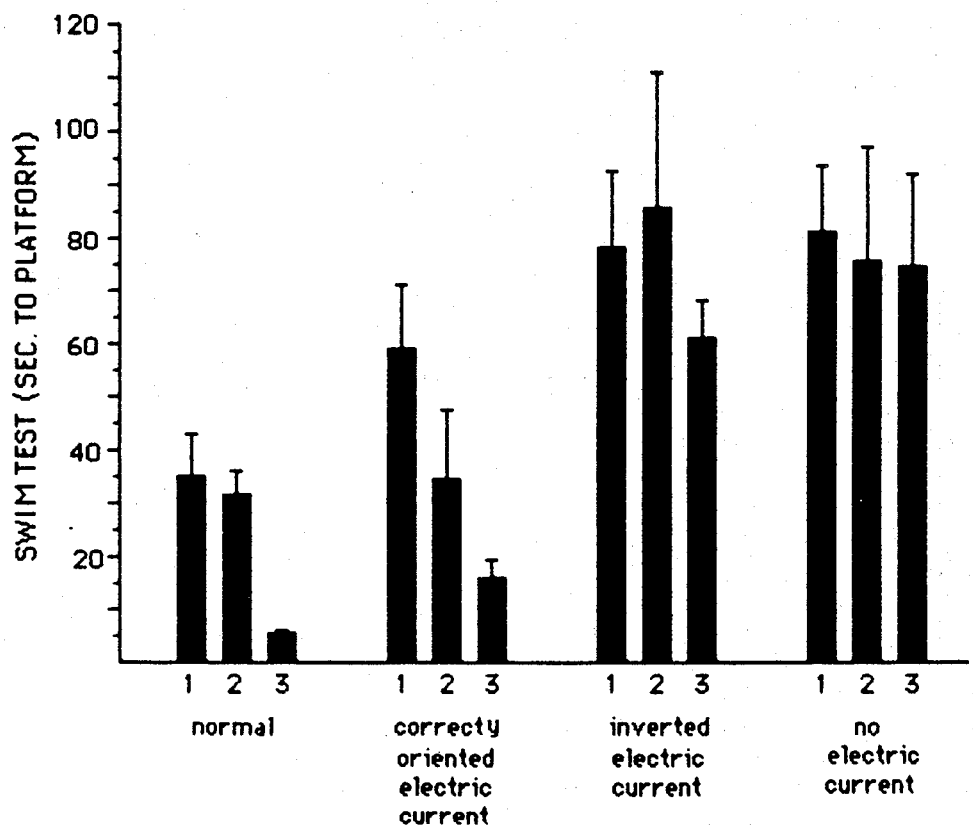

FIG. 9 shows a bar graph indicating the number of arm entries in fifteen minutes following four weeks of an implantation of apparatuses according to the invention in lesioned rat hippocampus with correctly oriented electric potential gradient, inverted electric potential gradient and no electric potential gradient, as compared to rats having no lesions and no implanted apparatuses (normal); and FIG. 10 shows a bar graph indicating Swim Test time in seconds after four weeks for rats following the implantation of the apparatuses according to the invention in lesioned rat hippocampus with correctly oriented electric potential gradient, inverted electric potential gradient and no electric potential gradient, as compared to rats having no lesions and no implanted apparatuses (normal).

DESCRIPTION OF THE INVENTION

Nerves can become damaged for many reasons such as physical impact, severing, or some other physical trauma. If the extent of the damage is limited, the damaged portion can be removed and the nerve ends can be easily abutted. For such a situation, it is convenient to suture the nerve ends together to maintain the nerve ends in substantial abutment to each other. This allows an implantable apparatus according to the invention to be used conveniently. The applicants have discovered that an electric potential gradient from the proximal nerve end to the distal nerve end can produce nerve regeneration for nerve ends which have been sutured together in contrast to the disclosure in the aforementioned U.S. Pat. No. 4,306,561. The regeneration of the nerve can require an extended application of the electric potential gradient and it is advantageous to have the apparatus in an implantable physical form so that the electric potential gradient can be maintained for a long period of time without having to maintain the subject either under operating conditions or immobile. Generally, the electric potential gradient is maintained for at least about a week and preferably for longer than about one month. A resultant electric current of about 1.5 microamps has been found satisfactory. The applied electric potential gradient is below the threshold voltage sufficient to elicit an action potential in the nerve. The range of suitable electric potential gradient amplitudes depends upon the nerves to be regenerated, the location of nerve injury, the subject, and the period of time the electric potential gradient is to be maintained. current depends upon the nerves to be regenerated, the location of nerve injury, the subject, and the period of time the electric current is to be maintained. These parameters can be based on data relating to in vitro experiments and can be determined experimentally.

In the case of extensive nerve damage, the removal of the damaged portion could result in the nerve ends being spaced apart a distance which does not allow the nerve ends to be brought into a abutment to each other without further nerve damage. In such a situation, it is advantageous to allow the nerve ends to be spaced apart while carrying out nerve growth and regeneration. It has been found that the growth of nerve ends spaced apart from each other under the influence of an electric current from the proximal nerve end to the distal nerve end will produce a regenerated nerve. A nerve guide means substantially improves the nerve regeneration process for both nerves sutured together or nerves spaced apart from each other.

It is preferable to have the apparatus according to the invention in an implantable physical form so that an electric potential gradient can be maintained with or without a nerve guide means for an extended period of time such as a week or several weeks or even longer while allowing the patient a minimum of discomfort. The electrical for producing electric potential gradient current according to the invention, in its simplest embodiment includes an electric cell and two wires connected to the terminals of the electric cell. The electric cell can be a commercially available miniature battery such as a battery used for hearing aids. One suitable electric cell is a type 13M miniature disc battery which has thickness of about 5 millimeters and a diameter of about 7 millimeters and produces a voltage of about 1.4 volts, well below the threshold voltage sufficient to elicit an action potential in any nerve. The wire used is preferably made of a metal compatible with a living body. One suitable metal is stainless steel. Preferably, the wires are insulated except for the portions to be used to produce the electric current through the damaged nerve. The insulating material is preferably compatible with a living body. One suitable insulating material is the material having the trademark TEFLON. Preferably, the wire is thin and typically has a diameter of about 35 microns. It is preferable to include a resistor in series with the electric cell in order to limit the electric current to a predetermined amount. The prior art includes many references stating the range of electric potential gradient used for in vitro experiments and this provides a guide for the level of electric potential gradient which may be suitable for in vivo mammalian nerve regenerating according to the invention. The generally maximum electric potential gradient used for the examples herein is well below the threshold voltage sufficient to elicit an action potential in the nerve and was determined by having the electric of the electric potential gradient and the wires completed with the wire ends in a physiological saline environment and measuring the electric current. From this data a resistor was selected so that the electric current for this situation would be about 1.5 microamps. The resistor used had a resistance of about 1 megohm. The battery and resistor are preferably placed into a form suitable for implanting. The battery and resistor with the wires attached can be encased in several layers of an epoxy and then the epoxy was covered with a medical grade adhesive, such as sold under the trademark of SILASTIC. It is known that SILASTIC minimizes tissue reaction to an implanted substance.

It is preferable to use the instant apparatus including a nerve guide means because the nerve guide means serves several important functions including maintaining the electrodes separated from each other, providing a convenient structure for contacting the wires with the respective nerve ends and providing a desirable environment for the growth and regeneration of nerves. Many nerves have a generally circular cross-section so that a nerve guide means in the form of a hollow circular cylinder is suitable for nerve regeneration of many types of nerves. The diameter of the inside cross section depends on the cross section of the nerve. The hollow central portion of the cylinder can be some other shape better adapted for the cross-sectional shape of the nerve. In practice, it is often necessary to engage the cylinder onto the nerve and later on to remove the cylinder. A slit or cut from one end to the other end of the cylinder will allow the cylinder to be spread open for these operations. A conventional surgical tool can be used to engage and remove the cylinder. The nerve guide means can also have the shape of an incomplete tube open at one side to simplify the engagement and disengagement of the tube. In some circumstances, such as nerves in the central nervous system in the spinal column, or brain, a nerve guide means in the form of a tube may not be convenient. For such a situation, a nerve guide means in the form of a curved plate can be used. The plate can be held in place by the use of sutures to enable implanting.

Referring now to FIGS. 1-4, an apparatus according to one embodiment of the invention is generally designated by the numeral 20. The apparatus 20 is shown in FIG. 1 engaged with a nerve 22 in a hand 24 during an operation to implant the apparatus 20. The apparatus 20 includes a combined battery and resistor 26, insulated wires 28 and 30 and a hollow cylinder 32 which serves as a nerve guide means. The cylinder 32 has a cut 34 from one end to the other end of the cylinder 32 so that the cylinder 32 can be opened with a conventional surgical tool (not shown) as shown in FIG. 2 to engage or disengage the nerve 22. Typically, the cylinder 32 is about 0.5 in. long, has an inside diameter of about 0.16 in. and an outside diameter of about 0.24 in. but this can be varied in accordance with the size of the nerve.

FIG. 2 shows the proximal nerve end 36 sutured to the distal nerve end 38 by sutures 40 so that the nerve ends 36 and 38 are substantially abutting each other. It can be seen in FIG. 3, the cylinder 32 engages the nerve 22 so that the sutured nerve ends 36 and 38 are within the cylinder 32. Preferably, the sutured nerve ends 36 and 38 are centrally positioned in the cylinder 32. The procedure for implanting the apparatus 20 into the hand 24 can be done using conventional techniques. FIG. 1 shows the use of a conventional surgical tool 42 (shown in part) for maintaining the hand 24 opened to receive the apparatus 20. The diameter of the cylinder 32 is selected so that it closely engages the nerve 22 without damaging the nerve 22. FIG. 4 shows a cross sectional view of the nerve 22 in the cylinder 32 as seen along the lines 4—4 in FIG. 3. As best seen FIGS. 2 and 3, the insulated wire 28 ends in a bare wire 44 which extends through a small hole in the wall of the cylinder 32 into the interior of the cylinder 32 so that it can electrically contact the proximal nerve end 36. Similarly, the insulated wire 30 has a bare wire end 46 which extends through a hole in the wall of the cylinder 32 into the interior of the cylinder 32 so that it can electrically contact the distal nerve end 38. The bare wire ends 44 and 46 can be fixed in position by the use of a suitable bonding agent such as SILASTIC sold by Dow Chemical Co.

FIG. 5 shows a sectional view of an apparatus 50 which is another embodiment of the invention. The apparatus 50 includes a hollow cylinder 52 serving as a nerve guide means with a cylinder 54 generally bonded perpendicular to the cylinder 52 using SILASTIC. As used in the example herein, the cylinder 52 is referred to the "nerve guide tube" and the cylinder 54 is referred to as the "lead tube." A battery and resistor (not shown) have insulated wires 56 and 58 extending down the cylinder 54 and out through holes 60 and 62 respectively. The wire 56 has a bare end 64 extending through a hole 66 in the cylinder 52 into the interior of the cylinder 52 to make electrical contact with a nerve end 68. Similarly, the insulated wire 54 has a bare wire end 70 which extends through a hole 74 in the cylinder 52 to the interior of the cylinder 52 to make electrical contact with nerve end 72. Nerve ends 68 and 72 are spaced apart from each other.

FIG. 6 shows a further embodiment of the invention in which a plate 80 is used as a nerve guide means and to maintain ends of wires 82 and 84 spaced apart and in contact with nerve ends (not shown). A combined battery and resistor 86 provides an electric potential gradient across the damaged nerve in order to enhance regeneration of the damaged nerve.

Apparatuses according to the invention as shown in FIG. 5 were implanted in rats and measurements were made to evaluate the performance of the apparatuses. Adult male Sprague-Dawley rats weighing approximately 300 g were used. Prior to sterile surgery, a KETAMINE anesthesia is administered to the rats (100 mg/100 g body weight, supplemented with ROMPUN). The implantation of the apparatuses are performed by a variation of the method disclosed in an apparatus by M. Politis and P. S. Spencer which appeared in "Brain Research", Vol 278, pp. 229-231, 1983. The nerve guide tube (corresponding to the cylinder 52) is placed near the nerve to be used, and the lead tube (corresponding to the cylinder 54) is sutured to the musculature in order to provide mechanical stability during manipulation. Thereafter, using a small scissors, the nerve is transected just before the first bifurcation of the sciatic nerve. This is an ideal location to transect the nerve because it allows maximum manipulation of the nerve while being distal enough to avoid severely traumatizing the perikarya. One centimeter of the distal stump is frozen on dry ice, allowed to thaw and then sutured to the proximal stump using 9-0 silk. The nerve guide tube was place over the sutured nerve. The lead tube is then further sutured to the musculature to provide additional mechanical stability. A long incision is made from the original thigh incision to extend to the dorsal aspect of the lower lumbar region. The power supply is fastened to the dorsal fascia with 5-0 silk. Each lead tube is gently fastened to the overlying fascia with 8-0 silk ligatures for additional stability. The skin overlying the power supply is then sutured closed.

Figure 7:
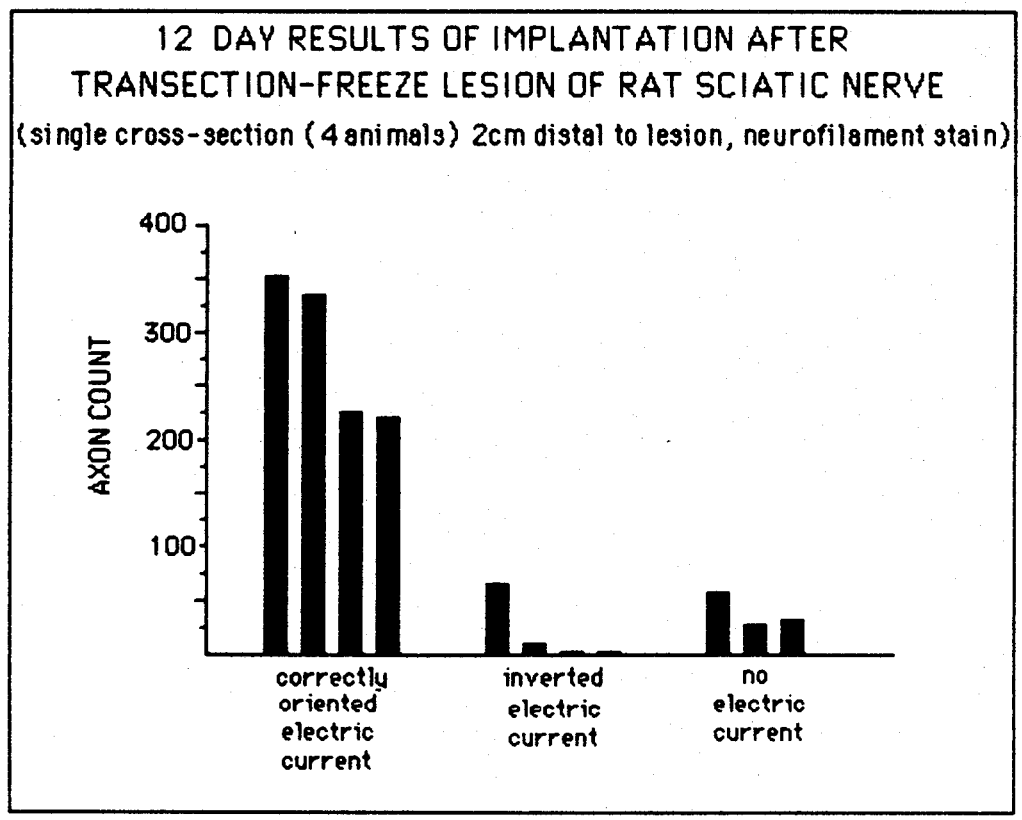
FIG. 7 is a bar graph showing axon count after twelve days for rats having implanted apparatuses according to the invention with correctly oriented electric potential gradient, inverted electric potential gradient, and no electric potential gradient being applied to the electrodes in the apparatuses.

FIG. 7 shows the results of implantation of apparatuses after transection-freeze lesion of rat sciatic nerves described above for three groups, each containing four rats. In one group of rats, correctly oriented potential gradient was used. In a second group of rats, the potential gradient was reversed and in a third group of rats no electric potential was used. The axon count in the distal stump was consistently higher for rats having apparatuses according to the invention using correctly oriented electric potential as compared to rats having apparatuses which had inverted electric potential or no electric potential.

Apparatuses according to the invention as shown in FIG. 6 were implanted in rats and measurements were made to evaluate the performance of the apparatuses to facilitate functional recovery in rats following severe brain injury. For this purpose, the medial fimbria bundle which contains cholinergic efferents projecting from the septum to dorsal hippocampus were unilaterly damaged. This partial-lesion paradigm reproducibly results in significant biochemical and behavioral deficits. The following is a more detailed description of the operation and subsequent evaluation.

Adult male Sprague-Dawley rats weighing approximately 300 g are anesthetized with NEMBUTAL anesthesia. The scalp and underlining fascia is resected to expose the skull. A 5 mm square bone flap is cut posterior to bregma and over the left hemisphere lateral to the midline (sagittal) suture. Approximately 3 mm square area of cortex is carefully removed by suction and the newly exposed underlining corpus callosum is gently resected until the head of the hippocampus is visible through a dissecting microscope. A pair of fine surgical forceps is placed just anterior to the exposed head of the hippocampus and inserted 1.5 mm into the brain. The tips of the fine forceps are then closed and opened several times, thereby crushing the medial fimbria bundle which projects from the septum to the hippocampus. After completion of the injury to the medial fimbria bundle, the embodiment of the invention as shown in FIG. 6 having dimensions of 2.5 mm wide and 4.5 mm long was inserted through the opening and slid into place so as to rest in the ventricular space just above the hippocampus. For rats having correctly oriented electric potential gradient, the cathode is positioned posteriorly over the dorsal hippocampus with the anode being 1mm rostral to the crushed medial fimbria bundle. For rats having inverted electric potential gradient, the implant is inverted with the cathode rostral and the anode caudal. This is also done for the rats which would have no electric potential gradient. The implants are anchored in place with GEL-FOAM packing and the electrical leads are run to the skull opening to the back of the neck where the attached battery power unit was subcutaneously sutured to the musclature. The facia and skin openings are then brought into apposition and sutured in place.

Four weeks after the implantation, measurements were carried out to evaluate the rats having brain implants as compared to rats having no lesions and no implants. Two conventional behavioral paradigms were used: the Y-Maze Test and the Swim Test. The Y-Maze Test is carried out by placing a rat in the center of three arms or paths and observing the number of times the rat enters one of the three arms as well as the specific sequence of arms entered over a fifteen minute test period. The total number of arms entered is indicative of the degree of overall behavioral activity and the percent of spontaneous alternations (in which the rat enters a new or different arm on consecutive trials from the center position as opposed to repeatedly reentering the same arm) is considered to be indicative of learning and memory. The Swin Test is another learning and memory dependent paradigm in which the rat is placed at the same starting position in a large body of water and is forced to swim around until it finds a single fixed platform. The rat is placed in the Swim Test apparatus for one trial per day and is allowed to swim until the platform is found and it can climb out of the water onto the platform or is placed on to another platform after a maximum time of 180 seconds has passed. The Swim Test was conducted on three successive days.

Figure 8:
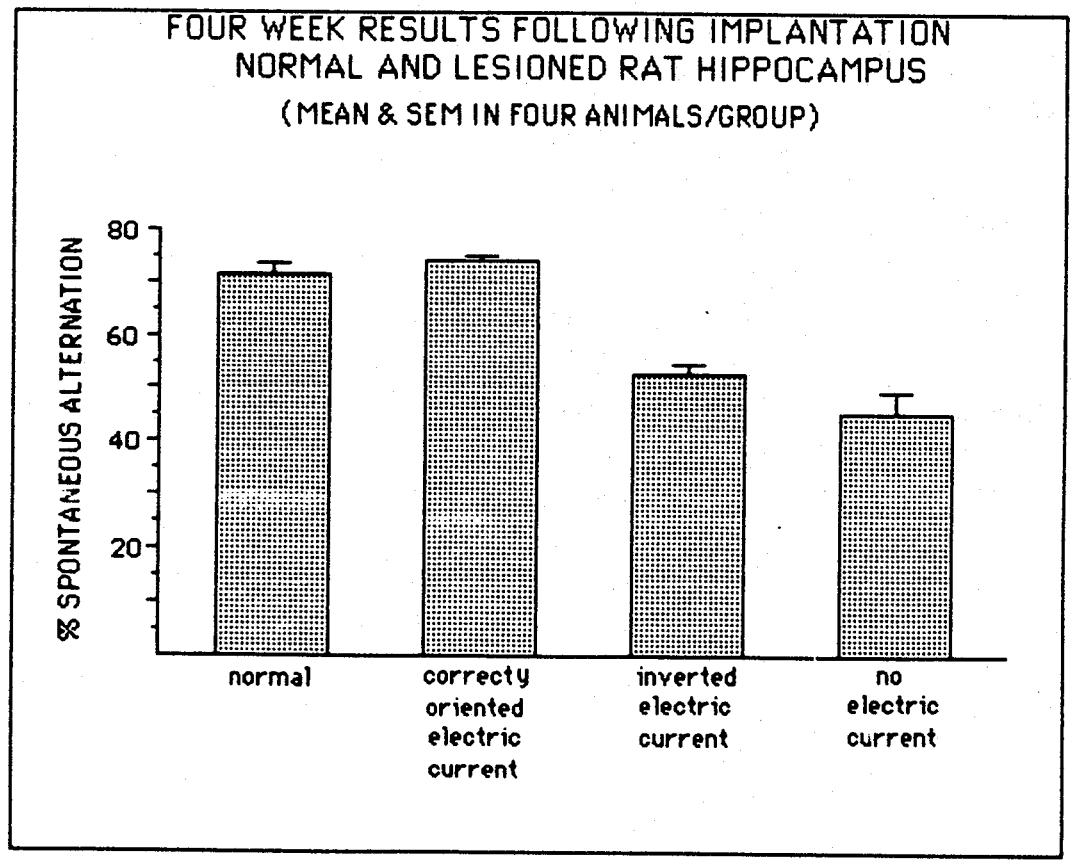
FIG. 8 shows a bar graph indicating percent of spontaneous alternation after four weeks for rats having implanted apparatuses in the brain according to the invention with correctly oriented electric potential gradient, inverted electric potential gradient and no electric potential gradient, as comapred to rats having no lesions and no implanted apparatuses (normal)

FIGS. 8, 9 and 10 show the results of the Y-Maze Test and Swim Test paradigms conducted with rats having brain implants with correctly oriented electric potential gradient, inverted electric potential gradient or no electric potential gradient as compared to normal rats. FIG. 8 shows the percent of spontaneous alternations for the Y-Maze Test. The rats having brain implants with inverted or no electric potential gradients had a lower percentage of spontaneous alternations than the rats having brain implants with correctly oriented electric potential gradients and normal rats. FIG. 9 is also the results of the Y-Maze Test and indicates a significantly greater number of arm entries for rats having brain implants with inverted electric potential gradients or no electric potential gradients as compared to rats having brain implants with currectly oriented electric current and normal rats. FIG. 10 shows the results of the Swim Test. The normal rats and the rats with the brain implants with correctly oriented electric potential gradients had latencies to the platform of 35 and 60 seconds respectively on the first test trials, but this latency improved to 7 and 17 seconds respectively by the third trials. This learning curve as indicated by the intermediate values for the second trials was not observed for the brain implanted rats having inverted electric potential gradient or no electric potential gradient. Moreover, the mean latency for the third test trials for the rats having brain implants with inverted electric potential gradient or no electric potential gradient still exceeded the slowest latencies observed during the first trial for the normal rats and the rats having brain implants with correctly oriented electric potential gradient.

After completion of the behavioral paradigms, the rats were sacrificed for the biochemical assessment of the level of acetylcholinesterase (AChE) activity in the left hippocampus. After the rats are sacrificed, the brains are quickly removed from the skulls and are sagittally transected into two hemispheres. The left hemisphere is placed over ice and the left dorsal hippocampus is dissected out. The head of the hippocampus is the site closest to the injury. Any remaining portion of the ventral-most hippocampus is trimmed away and the remaining body of the dorsal hippocampus is equally divided in half along the naso-temporal axis. The nasomost, or rostral/proximal portion, is known to receive the greatest percentage of cholinergic innervation from the medial fimbria. The resulting naso-section and temporal section of hippocampus is then homogenized and the level of AChE activity is assayed by routine spectrophotometric techniques. The results were analyzed in terms of absolute AChE values expressed as mg/ml of wet weight and as a percentage of control AChE activity from the normal rats.

Biochemical assay and analysis is only performed in the lesioned or left hemisphere because other studies have demonstrated that analysis of the contralateral side often yields variable results and is not an adequate internal control. The adequacy of the medial fimbria crushed lesions was verified by the significant AChE depletion in both absolute and percent of control values for the naso- and temporal hippocampal sections for all the lesioned rats. The rats having brain implants with correctly oriented electric potential gradient had greater AChE activity in the naso-section (65%) and temporal section (72%) than observed in the rats having brain implants with inverted electric potential gradient or no electric potential gradient, which averaged about 50% for both sections. Thus, the brain implants according to the invention partially reversed or prevented the functional deficits that ordinarily follow partial brain lesion. It can be concluded that the implant according to the invention is efficacious for the repair of the lesioned brain even though the lesion of the medial fimbria still resulted in biochemical and behavioral deficits because the treatment was a relatively short period of time of four weeks.

Experiments have also been conducted for regenerating optic nerves. In separate experiments, sixteen apparatuses according to the invention were constructed. These apparatuses provided a discrete distribution of electric potential gradient locally on a nerve. In each experiment, rats with optic nerve lesions were implanted with apparatuses according to the invention. The animals were allowed to survive for four weeks after the implantation. Afterwards, all of the animals were sacrificed and the tissue 2.5 mm distal to the lesion was processed for histological analysis by light microscopy (LM) using toluidine blue as well as neurofilament-specific staining. The results in every experimental animal showed that all of the animals implanted with apparatuses and correctly oriented potential gradient exhibited significant ingrowth of axons through and beyond the lesions, as compared to control optic nerves having apparatuses without electric potential gradient, or with reverse electric potential gradient. The optic nerves with apparatuses with correctly oriented potential gradient contained a significant number of myelin figures (averaging between 175 to 380 in each experiment), and reorganization of the tissue matrix including increased vascularity was apparent. All of the control optic nerves showed signs of debris and degeneration, and no indication of myelin figures. Whether the fibers observed in these experiments were regenerated optic fibers or re-routed peripheral fibers was addressed in other experiments. Ten animals were implanted with apparatuses according to the invention with correctly oriented electric potential gradient on the right optic nerves. After two weeks, the retinae of five of the animals were avulsed, and the animals were allowed to survive for two more weeks. At that time, the avulsed and non-avulsed animals were sacrificed and the optic nerves analyzed as described above. In the non-avulsed animals, all optic nerves showed regenerating axons in the region distal to the lesion as in previous studies. Four of the five avulsed animals showed no signs of regenerating axons, indicating that removal of the retina destroys the complement of axons. Thus, in these animals, the CNS (in this case, ganglion cells) could be made to regenerate through a lesion and extend into the distal portion of the nerve.

Although the invention herein has been described with reference to particular embodiments, it is to be understood that these embodiments are merely illustrative of the principal and application of the invention. Thus, it is to be understood that numerous modifications may be made in the illustrative embodiments and other arrangements may be devised without departing from the spirit and scope of the invention.

We claim:

1. An apparatus for in vivo regeneration of a damaged mammalian nerve having proximal and distal nerve ends comprising alignment means extending over said proximal and distal nerve ends for maintaining the nerve ends in proximity to each other and means coupled to said alignment means adapted for applying an electric potential gradient between the proximal nerve end and the distal nerve end at a level, direction and for a period of time to produce nerve regeneration.

2. The apparatus of claim 1, wherein said means adapted for applying an electric potential gradient includes a battery which establishes a higher electric potential at the proximal nerve end relative to the distal nerve end.

3. The apparatus of claim 1, wherein said alignment means for maintaining the nerve ends in proximity includes a nerve guide having a hollow tube for receiving said proximal and distal nerve ends.

4. An appartus at least partially implantable in a human body for regenerating a damaged nerve having proximal and distal nerve ends comprising nerve guide means adapted to extend over said proximal and distal nerve ends for maintaining said nerve ends in juxtaposition with one another, and means coupled to said nerve guide means adapted for applying an electric potential gradient between the nerve ends with a higher potential at the proximal nerve end and a lower potential at the distal nerve end for a time and at a level to produce nerve regeneration.

5. An apparatus for in vivo regeneration of a damaged mammalian nerve having proximal and distal nerve ends comprising a nerve guide means adapted to extend over said proximal and distal nerve ends for maintaining said nerve ends in juxtaposition with one another and means coupled to said nerve guide means adapted for applying a potential gradient between the nerve ends at a level below the threshold for establishing action potential in said nerve and in a direction and for a time to produce nerve regeneration.

6. The apparatus of claim 5, wherein said means for applying a potential gradient includes means for establishing a higher potential at the proximal nerve and relative to the distal nerve end.

7. An apparatus for regenerating a damaged nerve having proximal and distal nerve ends comprising nerve guide means implantable in the human body and extending over said proximal and distal nerve ends for maintaining said nerve ends in juxtaposition with one another, and means coupled to said nerve guide means for establishing an electric potential gradient between the nerve ends with a higher potential at the proximal nerve end relative to the distal nerve end and at a level below the threshold for establishing action potential in the nerve and for a time sufficient to produce regeneration of the damaged nerve.

8. A method of in vivo regeneration of a damaged mammalian nerve having proximal and distal nerve ends comprising bringing said proximal and distal nerve ends into proximity with each other and thereafter establishing an electric potential gradient between the proximal nerve end and the distal nerve end at a level and for a period of time to produce nerve regeneration.

9. The method of claim 8, wherein said electric potential is greater at the proximal nerve and relative to the distal nerve end.

10. The method of claim 9, wherein the level of said electric potential gradient is below the threshold for establishing action potential in said nerve.

11. A method of mammalian nerve regeneration of a damaged nerve having proximal and distal nerve ends comprising implanting a nerve guide means over the proximal and distal nerve ends to maintain said nerve ends in juxtaposition with one another and applying an electric potential gradient between said proximal nerve end and said distal nerve end with the electric potential being higher at the proximal nerve end, said potential gradient being below the threshold for establishing action potential in the nerve, and being applied for a period of time necessary to produce nerve regeneration.

12. The method of claim 11, wherein the electric potential is applied for at least one week.

13. A method of in vivo regeneration of a damaged mammalian nerve having proximal and distal nerve ends comprising positioning a nerve guide means proximate the damaged nerve to bring said proximal and distal nerve ends into proximity with each other, suturing said proximal and distal nerve ends together and thereafter applying an electric potential gradient between the proximal nerve end and the distal nerve end at a level and for a period of time to produce nerve regeneration

* * * * *